(12) United States Patent
Jensen et al.

(10) Patent No.: US 6,391,283 B1
(45) Date of Patent: *May 21, 2002

(54) METHODS AND APPARATUS FOR ACTIVATING DENTAL COMPOSITIONS

(75) Inventors: Steven D. Jensen, Riverton; Dan E. Fischer, Sandy, both of UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/010,155

(22) Filed: Jan. 21, 1998

Related U.S. Application Data

(63) Continuation-in-part of application No. 08/781,662, filed on Jan. 10, 1997, now Pat. No. 5,785,527, and a continuation-in-part of application No. 08/781,858, filed on Jan. 10, 1997, now Pat. No. 5,858,332.

(51) Int. Cl.[7] .................................................. A61K 7/16
(52) U.S. Cl. .............................. 424/49; 424/53; 433/215
(58) Field of Search ............................ 424/49, 53, 613, 424/616; 252/186.38, 186.41; 433/215, 29

(56) References Cited

U.S. PATENT DOCUMENTS

| | | | | |
|---|---|---|---|---|
| 3,949,477 A | | 4/1976 | Cohen et al. ................. 32/14 A |
| 4,952,143 A | | 8/1990 | Becker et al. ................. 433/32 |
| 5,316,473 A | * | 5/1994 | Hare ............................. 433/29 |
| 5,487,662 A | * | 1/1996 | Kipke et al. .................. 433/37 |
| 5,683,679 A | * | 11/1997 | Sharma ......................... 424/53 |
| 5,713,738 A | * | 2/1998 | Yarborough ................. 433/215 |
| 5,785,527 A | * | 7/1998 | Jensen et al. ................ 433/215 |
| 5,813,854 A | | 9/1998 | Nikodem ...................... 433/29 |
| 5,879,159 A | * | 3/1999 | Cipolla ......................... 433/29 |
| 6,036,493 A | * | 3/2000 | Sharma ....................... 433/216 |
| 6,108,293 A | * | 8/2000 | Wiesel ........................ 433/215 |

FOREIGN PATENT DOCUMENTS

| | | | |
|---|---|---|---|
| EP | 0 105 747 | * | 4/1984 |
| WO | WO 00/16737 | * | 3/2000 |

OTHER PUBLICATIONS

Strassler H. Whitening. RDH 17(6)24–28, 30, Jun. 1997.*
Thompson K. Mechanism of Peroxide Bleaching at High pH. J Chem Soc (21)1600–1, 1992.*
Thompson K. Mechanism Bleaching by Peroxides. J. Chem Soc Faraday Trans 89(22)4035–4043, 1993.*
Kotkowski S. Some Physico–Chemical Properties of Food Dyes. Rocz Panstw Zakl Hig 19(1)69–68, Jan. 1968.*

* cited by examiner

*Primary Examiner*—Ralph Gitomer
(74) *Attorney, Agent, or Firm*—Workman, Nydegger, Seeley

(57) ABSTRACT

Compositions, method and systems for bleaching tooth surfaces in an accelerated manner. The dental bleaching compositions include a bleaching agent and a stable radiant energy absorbing material that acts as a bleaching agent activator. The dental bleaching compositions of the present invention can be stable one-part compositions that do not require mixing at the time of treating a person's teeth but which remain stable over time. The dental bleaching composition is applied to the labial surface of teeth that are to be bleached. A source of radiant energy is directed onto the treated tooth surfaces to accelerate bleaching activity. The radiant energy source includes a dental light guide having an arcuate light directing member that is positioned in close proximity to the treated teeth. The light directing member has one or more light-emitting panels communicating with a radiant energy generating source that efficiently direct radiant energy onto the treated tooth surfaces. The dental light guide can irradiate all treated teeth of one or both dental arches simultaneously while in a fixed position relative to the one or both dental arches. The inventive dental compositions may also be activated using, e.g., conventional curing lights and lasers.

21 Claims, 3 Drawing Sheets

METHODS AND APPARATUS FOR ACTIVATING DENTAL COMPOSITIONS

RELATED APPLICATIONS

This application is a continuation-in-part of copending U.S. application Ser. No. 08/781,662, entitled "Stable Light Or Heat Activated Dental Bleaching Compositions" and filed Jan. 10, 1997 in the names of Steven D. Jensen and Dan E. Fischer now U.S. Pat No. 5,785,527 and also a continuation-in-part of copending U.S. application Ser. No. 08/781,858, entitled "Dental Bleaching Compositions With High Concentrations Of Hydrogen Peroxide" and filed Jan. 10, 1997 Now U.S. Pat. No. 5,858,332 in the names of Steven D. Jensen and Dan E. Fischer. For purposes of disclosure of the present invention, each of the foregoing applications is incorporated herein by specific reference.

BACKGROUND OF THE INVENTION

1. The Field of the Invention

The present invention relates to methods and systems for treating tooth surfaces. More particularly, the present invention is directed to methods and systems for activating dental bleaching compositions on a person's teeth. The methods and systems for activating the bleaching compositions utilize a dental light guide configured to focus radiant energy on the person's teeth being treated.

2. Relevant Technology

The use of certain foods and tobacco, the process of aging, diseases, trauma, medications, some congenital conditions, and environmental effects can cause teeth to become discolored. Because white or whitened teeth are usually considered to be aesthetically superior to stained or discolored teeth, there has been a heightened level of interest of late in developing compositions and methods for bleaching teeth.

A tooth is comprised of an inner dentin layer and an outer hard enamel layer that is slightly porous. The outer layer is the protective layer of the tooth. The natural color of the tooth is opaque to translucent white or slightly off-white.

Some dentifrices, like toothpastes, gels, and powders contain active oxygen or hydrogen peroxide liberating bleaching agents. Such bleaching agents include peroxides, percarbonates and perborates of the alkali and alkaline earth metals or complex compounds containing hydrogen peroxide. Also, peroxide salts of the alkali or alkaline earth metals are known to be useful in whitening teeth.

The most commonly used dental bleaching agent is carbamide peroxide ($CO(NH_2)_2 \cdot H_2O_2$), also called urea hydrogen peroxide, hydrogen peroxide carbamide, and perhydrolurea. Carbamide peroxide has been used by dental clinicians for several decades as an oral antiseptic. Tooth bleaching was an observed side effect of extended contact time. Over-the-counter compositions of 10% carbamide peroxide are available as "GLY-OXIDE®" by Marion Laboratories and "PROXIGEL®" by Reed and Carnrick. An extended-contact application of bleaching gel held in a dental tray is available as "OPALESCENCE®" by Ultradent. Other bleaching agents such as peroxyacetic acid ($CH_3C=OO—OH$) and sodium perborate, are also known in the medical, dental and cosmetic arts.

People who have desired to have their teeth whitened have typically done so by applying a bleaching composition to the teeth by means of the dental tray for repeated treatments, or they had to submit to conventional in-office bleaching techniques that required from 4 to 10 visits to the dental office before clinically significant results were achieved. Less effective teeth whitening was also done by the use of toothpastes or polishes that were applied by brushing. Clinically significant results are quantifiable such as by measuring gray scale, L*, and as to yellowness or blueness, b*, in the CIE® system of color measurement or by equivalent methods.

Bleaching compositions have been manufactured in one-part and two-part systems. A one-part system consists of a compound in which the active bleachant is dispersed into inert components to form an emulsion or gel. One-part systems can also further consist of mixtures in which stabilizers are used to prevent premature decomposition of the peroxide in the bleaching composition. The advantage of a one-part system is ease of use and convenience. The main disadvantage is that prior art one-part bleaching compositions generally contain relatively low concentrations of peroxide due to the instability of more highly concentrated peroxide compositions. Thus, current one-part systems have a low potency and are slow to react. Most one-part systems in the past have included active peroxide in a range of up to about 3.5% by weight. Due to the relatively low concentration of active bleaching agent in one-part systems, about 10 applications on average are necessary for effective bleaching.

In a two-part system, aqueous hydrogen peroxide is stabilized in a first part, while activators (i.e., destabilizers) are contained in a second part. These components are mixed just prior to bleaching in order to cause decomposition (i.e., activation) of the hydrogen peroxide at the time of use. The main advantage of a two-part system is that it allows for much higher concentrations of active peroxide that cannot exist stably as a one-part system for incidental off-the-shelf use. This results in faster bleaching of the person's teeth due to the higher peroxide concentration. Faster bleaching is desirable, especially where the person undergoing treatment finds it difficult to comply with longer bleaching regimens, or if only one or a few teeth need bleaching. A disadvantage of two-part systems is the inconvenience of having to mix the components just prior to use.

Another example of a two-part system is microencapsulation of the bleaching agent and a stabilizer. The microcapsules would separate the bleaching agent from the carrier and other materials and would rupture only upon physical shear caused by a tooth brush. Like other one-part systems, the dental bleaching effect of the microencapsulation system is only visible after prolonged use due to its low peroxide concentration or low activation rate.

Although positive results using the foregoing techniques have been reported, the effectiveness of the techniques depends upon such factors as type and intensity of the stain, bleaching agent contact time on the teeth, the amount of available active bleachant in the bleaching agent, and the persistence of the individual in applying the treatment until the desired result is accomplished.

Notwithstanding the foregoing advantages, there remain some important disadvantages to current one-part and two-part systems. A disadvantage to the two-part system is that the bleaching composition must be mixed on-site in the operatory immediately before application to the person's tooth. Mixing requires additional time by the dental professional, which lowers efficiency and represents an extra preparatory procedure. Mixing in proper amounts is also important in order to yield consistent results.

Another disadvantage with two-part bleaching compositions is that, once mixed, the bleaching compositions must be used soon, since they are unstable and tend to decompose through the release of oxygen from the peroxide moieties. Often, the constituents of the bleaching compositions themselves accelerate decomposition rates. While such accelerants are useful in promoting faster bleaching, they yield a composition having a very short lifespan. Because known accelerants are chemical in nature, they cannot be added until bleaching is to commence. Otherwise the premature release of active oxygen will quickly decrease the potency of the bleaching composition. Moreover some accelerants or peroxide indicators reduce bleaching ability since they themselves consume the peroxide, thus competing with the teeth for the peroxide.

In view of the foregoing, it will be appreciated that what is needed in the art are methods of treating tooth surfaces with stable, one-part dental bleaching compositions that allow for greatly increased bleaching rates compared to existing one-part systems.

Additionally, it would be a significant advancement in the art to provide methods for treating tooth surfaces with stable, one-part dental bleaching compositions that included means for triggering or accelerating the release of active oxygen from the bleaching agent when needed but which did not cause premature decomposition of the active dental bleaching agent or destruction of the bleaching agent activator prior to use.

It would be a further advancement in the art to provide methods for treating tooth surfaces with stable, one-part dental bleaching compositions that include higher concentrations of bleaching agent compared to existing one-part compositions.

There is also a need in the art to provide methods for treating tooth surfaces with a dental bleaching composition that included an agent that could cause accelerated activation of the bleaching agent upon irradiating the dental bleaching composition with radiant energy.

It would be yet another advancement in the art to provide methods and systems for increasing the rate of bleaching activity of a dental bleaching composition by directing radiant energy simultaneously over the entire area of teeth to be treated without having to redirect the radiant energy source to irradiate all of the teeth being treated.

It would further be an improvement in the art to provide methods and systems for increasing the rate of bleaching activity of a dental bleaching composition if the radiant energy could be more accurately focused onto the person's teeth to be treated rather than onto surrounding tissues, particularly sensitive oral tissues.

Such compositions, methods and systems for accelerated treatment of tooth surfaces with stable, one-part dental bleaching compositions are disclosed and claimed herein.

SUMMARY OF THE INVENTION

The present invention is directed to methods and systems for treating tooth surfaces with dental bleaching compositions, more particularly, stable one-part dental bleaching compositions having relatively high concentrations of a dental bleaching agent and a radiant-energy activating agent that acts to accelerate bleaching activity upon irradiating the dental bleaching composition with radiant energy. Hence, the bleaching rate of the bleaching composition is accelerated using an apparatus for directing radiant energy onto the tooth surfaces to be treated. The preferred apparatus is a novel dental light guide that is able to simultaneously direct radiant energy on a desired number of the teeth of a dental arch to be treated, while remaining in a substantially fixed position relative to the dental arch.

The dental bleaching compositions of the present invention include stable, one-part, pre-mixed compositions with a sufficient shelf life to allow for long-term storage and use as needed. Preferred bleaching agents include peroxides such as hydrogen peroxide and carbamide peroxide (which is a complex between urea and hydrogen peroxide). A thickening agent can be used to give the dental bleaching composition a desired consistency, stickiness, and viscosity. Preferred thickening agents include PEMULEN®, a proprietary compound from B.F. Goodrich, or a compositional or chemical equivalent thereof.

An important advantage of the preferred bleaching compositions of the present invention are that they are stable over time. A major cause of premature degradation of the bleaching agent is the existence of errant or residual metal ions that can act as bleaching agent catalysts. Hence, it is possible to create stable bleaching compositions even at high concentrations (greater than 20% by weight) by avoiding, removing, or trapping errant or residual metal ions. Scavenging of errant or residual metal ions can be accomplished by means of a bleaching agent stabilizer. The bleaching agent stabilizer comprises edetate disodium, EDTA, oxine EDTA, calcium disodium EDTA, adipic acid, succinic acid, citric acid, tin nitrates, tin phosphates, their respective salts, their combinations, and the like.

Activation of the dental bleaching composition of the present invention is accomplished with a bleaching agent activator that is preferably a radiant-energy or heat-energy absorbing substance. Examples of such substances include radiant-energy absorbing, substantially conjugated hydrocarbons such as aromatic hydrocarbons, multiple double-bond hydrocarbon chains, chain-aromatic mixtures, reacted combinations thereof, and equivalents. Specific examples include caroteneoids such as bixin, lycoxanthin, lycophil, canthaxanthin, capsanthin, cryptoxanthin, isomers of carotene, and lycopene. Other specific examples include aromatics such as coronene, fluoranthene, naphtho[2,3-a]pyrene, trans-4,4'-diphenylstilbene, 9,10-diphenylanthracene, 5,12-bis (phenyethynyl) napthacene, 9,10-bis (phenylethynyl) anthracene, and perylene. The foregoing compounds may optionally include one or more carboxyl groups. The only limitations are (1) that the radiarit-energy absorbing substance does not cause substantial peroxide decomposition over time, and (2) that the radiant-energy absorbing substance be relatively stable in the presence of the bleaching agent over time. Preferred bleaching agent activators include 9,10-bis (phenylethynyl) anthracene, perylene, and isomers of carotene and carboxyl-substituted variations thereof.

The inventive bleaching compositions preferably include an inert carrier, including but not limited to, water, polypropylene glycol, polyethylene glycol, sorbitol, propylene glycol, glycerol, steryl alcohol, large molecular weight polyols, mixtures of the foregoing, and equivalents.

Because the bleaching compositions of the present invention are both stable in a one-part, pre-mixed system and include the radiant-energy absorbing substance, the bleaching process is greatly simplified. The dental bleaching compositions may advantageously be either preloaded or loaded manually into and dispensed from a syringe onto the person's teeth. The dental professional simply expresses a desired quantity of the dental bleaching composition over the person's teeth to be treated and then triggers accelerated bleaching by either irradiating the bleaching composition with radiant energy, such as visible and/or UV light, or by applying, e.g., conductive heat energy to the composition before, during, or after application to the teeth. Depending on the desired rate of bleaching and sensitivity of the person undergoing treatment to bleaching agents, a bleaching composition having the optimum amount of bleaching agent can be selected before bleaching commences or can be determined by noting the results of the first bleaching treatment.

A preferred method of irradiating the bleaching composition involves using a dental light guide having an arcuate member that is configured such that a portion or all of a person's dental arch, including the treated teeth, may be positioned in close proximity to an inner surface thereof. The inner surface of the arcuate member has one or more light-emitting panels thereon in a location such that the labial surfaces of the treated teeth may be irradiated. The light guide further includes a light source and a plurality of optical fibers or other light-transmitting means to carry radiant energy to the light-emitting panels. The light guide can be configured to cover part or all of the upper dental arch, part or all of the lower dental arch, or part or all of both the upper and lower dental arches.

According to a preferred method of the invention, after the dental bleaching composition has been applied to the selected teeth, the light guide is introduced into the person's mouth such that the selected teeth are in close proximity to the arcuate member. The radiant energy source of the light guide is activated to cause radiant energy to pass through the light-emitting panels onto the treated teeth. The bleaching rate of the bleaching composition accelerates in response to the introduction of radiant energy in close proximity to the teeth being treated. The light guide is kept in place over the treated teeth until a desired amount of bleaching has occurred.

By use of the foregoing light guide, a practitioner may irradiate tooth surfaces without needing to redirect the light guide onto different teeth. Instead, the preferred light guide remains in a fixed position in relation to the dental arch. As a result, the practitioner may easily monitor the overall amount of time that the treated teeth are irradiated. Moreover, the amount of time that individual teeth are treated can easily be determined, thereby facilitating uniform bleaching. Simultaneously irradiating the complete set of treated teeth within a single dental arch decreases the length of the treatment session that would otherwise be required.

In view of the foregoing, it is an object of the present invention to provide methods for treating tooth surfaces with stable, one-part dental bleaching compositions that allow for greatly increased bleaching rates compared to existing one-part systems.

It is a further object and feature of the present invention to provide methods for treating tooth surfaces with stable, one-part, pre-mixed viscous/gelled dental bleaching compositions that include means for triggering or accelerating the release of active oxygen from the bleaching agent when needed but which does not cause premature decomposition of the active dental bleaching agent or destruction of the bleaching agent activator prior to use.

It is still a further object and feature of the present invention to provide methods for treating tooth surfaces with stable, one-part dental bleaching compositions that include higher concentrations of bleaching agent compared to existing one-part compositions.

It is a further object and feature of the present invention to provide methods for treating tooth surfaces with a dental bleaching composition that includes an agent that causes accelerated activation of the bleaching agent upon irradiating the dental bleaching composition with radiant energy.

It is yet another object and feature of the present invention to provide methods and systems for increasing the rate of bleaching activity of a dental bleaching composition by directing radiant energy simultaneously over the entire area of teeth to be treated without having to redirect the radiant energy source to irradiate all of the teeth being treated.

It is a further object to provide methods and systems for increasing the rate of bleaching activity of a dental bleaching composition where the radiant energy can be more accurately focused onto the person's teeth to be treated rather than onto surrounding tissues, particularly sensitive oral tissues.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
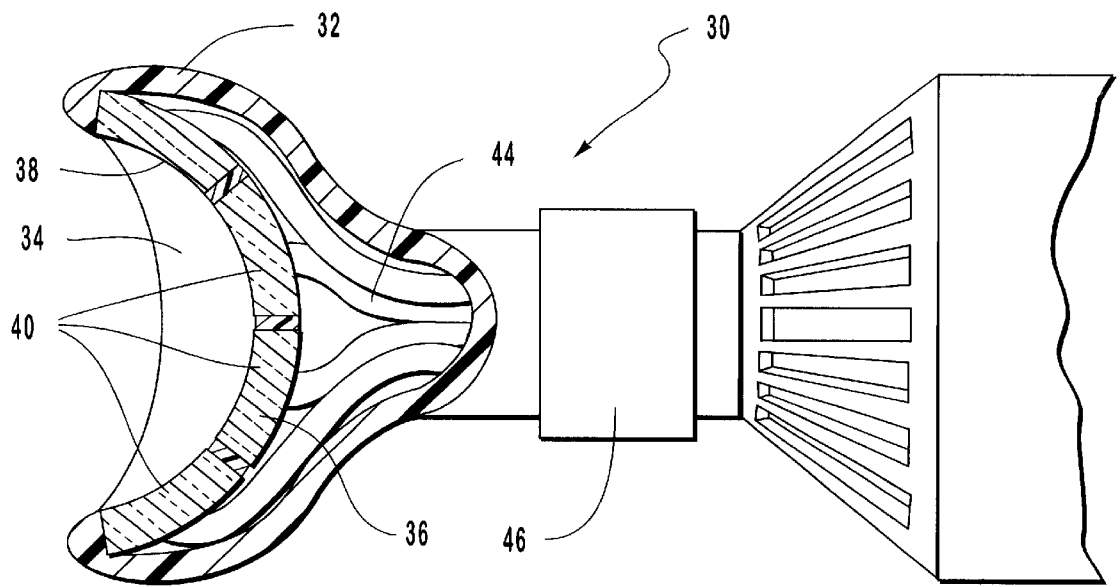
FIG. 1 is a top view of the light guide of the present invention. Optical fibers direct radiant energy to a plurality of light-transmitting panels arrayed upon a sidewall of an arcuate member.

The present invention comprises methods and systems for bleaching tooth surfaces. The inventive methods and systems can be used with conventional bleaching compositions; however, preferred dental bleaching compositions include stable, one-part, pre-mixed dental bleaching compositions having a bleaching agent and a radiant-energy absorbing constituent that acts as a bleaching agent activator. Typically, the bleaching composition is placed on at least the labial surfaces of one or more teeth. A radiant energy source is used to direct radiant energy onto the treated tooth surfaces. The bleaching agent activator causes the bleaching agent to become "activated" or caused to decompose more rapidly into bleaching constituents upon irradiating the bleaching composition with radiant energy.

A preferred apparatus for irradiating the treated tooth surfaces comprises a novel dental light guide that is able to simultaneously direct radiant energy on part or all of the teeth of a dental arch while remaining in a substantially fixed position relative to the dental arch. The light guide has an arcuate member that is configured so as to be placed in close proximity with the labial surfaces of the treated teeth. The arcuate member has an inner surface with at least one light-emitting panel positioned thereon such that radiant energy may pass through the light-emitting panel onto the treated tooth surfaces.

The method is carried out by introducing the arcuate member into the mouth of the person, with the light-emitting panels being placed in close proximity to the treated tooth surfaces. A light source interfacing with the light guide is activated to produce radiant energy, which is carried by means of optical fibers or other radiant transmitting means to the light-emitting panels in the light guide. The treated tooth surfaces are irradiated for a desired length of time until a suitable degree of bleaching has occurred. The arcuate member is then removed from the person's mouth. The foregoing method can be repeated as desired to obtain favorable results.

The terms "light" or "radiant energy", as used in the specification and the appended claims, refer to electromagnetic radiation. These terms include electromagnetic radiation having any wavelength with which the bleaching activity of a bleaching composition may be activated, increased, or accelerated. Thus, these terms include, but are not limited to, electromagnetic radiation in the visible, infrared and ultraviolet regions of the electromagnetic spectrum.

Preferred bleaching compositions and preferred light guides will be disclosed in greater detail below.

A. Bleaching Compositions.

The one-part, pre-mixed dental bleaching compositions of the present invention comprise several components that, working in concert, provide a stable and effective dental bleaching composition. The inventive bleaching compositions are stable over time while having the capability of being activated for accelerated bleaching by means of radiant light or heat energy. The components preferably include a bleaching agent, a thickening or gelling agent, a neutralizing agent, a carrier, a bleaching agent stabilizer, and a bleaching agent activator. Each component contributes to the dental bleaching composition in different ways.

1. Bleaching Agents.

Preferred bleaching agents include hydrogen peroxide and hydrogen peroxide-containing complexes and compounds, such as carbamide peroxide $(NH_2)_2CO \cdot H_2O_2$. Peroxides can provide a ready source of active oxygen in effective concentrations.

Hydrogen peroxide is the preferred bleaching agent in some cases, especially where it is desired to include a relatively high concentration of bleaching agent concentrations. Because of the nature of hydrogen peroxide, it is only available as an aqueous solution. Aqueous hydrogen peroxide solutions from 3% to 90% by weight hydrogen peroxide are commercially available.

On the other hand, carbamide peroxide can provide a nonaqueous form of available hydrogen peroxide. Carbamide peroxide in its pure form is a crystalline substance consisting of a molecule of urea complexed with a single molecule of hydrogen peroxide. Carbamide peroxide is generally more stable than aqueous hydrogen peroxide and is often preferred for that reason. However, because of the existence of the urea molecule, pure crystalline urea peroxide contains only about 36% available hydrogen peroxide. This means that the upper limit of available peroxide for bleaching when only using carbamide peroxide is lower than 36% when significant quantities of other components such as water, propylene glycol, or glycerol and the like are included in the bleaching composition.

The type and amount of hydrogen peroxide to be used will depend on the desired peroxide concentration in the final dental bleaching composition. In general, it will be preferable to use concentrated hydrogen peroxide solutions when it is desired to manufacture a bleaching composition having high concentrations of bleaching agent. Lower concentrated hydrogen peroxide solutions and/or carbamide peroxide and/or sodium perborate are generally used when it is desired to manufacture a bleaching composition having lower concentrations of bleaching agent. Carbamide peroxide solutions and hydrogen peroxide solutions can be mixed together in varying concentrations to yield bleaching compositions having a wide spectrum of bleaching agent concentrations. Additionally, sodium perborate can be used alone or it can be mixed with each or both of hydrogen peroxide and carbamide peroxide.

Because hydrogen peroxide is generally less stable with increasing pH, many hydrogen peroxide solutions include acidifying agents such as mineral acids in order to render a more stable hydrogen peroxide solution. However, upon mixing such solutions with the other constituents to yield the dental composition of the present invention, it will generally be desired to adjust the pH to an acceptable pH range in order to protect the person's teeth and surrounding tissues. The concept of pH adjustment will be discussed herein below. The concentration of hydrogen peroxide will preferably be in a range from about 0.1 to about 90% by weight of the dental composition, more preferably in a range from about 10% to about 80%, and most preferably in a range from about 20% to about 60% by weight.

2. Thickening Agents.

Thickening agents or gelling agents assist to increase viscosity, to facilitate ease of placement, and to assure the composition stays in place during treatment. Thus, thickening agents aid the composition to remain in place during treatment. Thickening agents preferably have the quality of being substantially inert in the presence of, and not readily decomposed by, the bleaching agent. It has been found that thickening agents that are substantially hydrophilic but have a relatively small lipophilic moiety, are preferred in the present invention. For example, a preferred thickening agent is an emulsifier comprising a high molecular weight polyacrylic acid polymer or copolymer.

As an example of a preferred thickening agent, we have found that PEMULEN® or a compositional or chemical equivalent thereof possesses the qualities required for the inventive composition. A more preferred thickening agent is PEMULEN® TR-1NF. PEMULEN® is a propriety formula that includes a significant quantity of a polyacrylic copolymer that has a slightly hydrophobic end and a strongly hydrophilic end.

3. Neutralizing Agents.

In light of the acidity of hydrogen peroxide stock solutions and some solutions of polyacrylic acid thickeners such as PEMULEN or a compositional or chemical equivalent thereof; it is usually desired to use a neutralizing agent to adjust the pH to within an acceptable pH range. Raising the pH causes some thickeners to become more viscous. In addition, bleaching compositions that are too acidic can etch the person's teeth and cause irritation to surrounding dental tissues. In most cases, the pH will be in a range from about 2 to about 9, more preferably in a range from about 3 to about 7, and most preferably from about 4 to about 6. Preferred neutralizing agents include alkali hydroxides, such as sodium hydroxide and potassium hydroxide, amines such as disopropanol amine and triethanol amine, ammonium hydroxide, and the like. The most preferred neutralizing agent is sodium hydroxide, 50 percent in distilled or deionized water.

4. Carriers.

The carrier is used to complement the other dental bleaching composition components and effect good dispersion and stability of the resulting compositions. By adjusting the amount of carrier the bleaching agent concentration can be adjusted to a selected level. The use of a carrier or carrier combinations aligned with a thickening agent allows for achievement of a selected bleaching agent concentration and a selected consistency. Water, or water in combination with other components including other carriers is sometimes used. Other carriers include polyols, such as polypropylene glycol, polyethylene glycol, sorbitol, propylene glycol, glycerol, ethylene glycol, large molecular weight polyols, and the like, and mixtures of the above. Although ethylene glycol could work as a carrier, it is not used because it is toxic. The carrier may comprise stearyl alcohol.

5. Bleaching Agent Stabilizers.

The bleaching agent stabilizers act as impurity scavengers that bind with errant or residual metal ions and other impurity elements that might cause decomposition of the bleaching agent. The stabilizer also must not itself be a source of bleaching agent instability. Where an excess of stabilizer is in solution such that all impurities have been bound up by the stabilizer, the excess stabilizer must itself be inert to the bleaching agent. At least two classes of bleaching agent stabilizers are part of the present invention. One class comprises carboxylic acid chelators, such as edetate disodium, EDTA, oxine EDTA, calcium disodium EDTA, adipic acid, succinic acid, citric acid, and the like and mixtures thereof, their respective salts or derivatives. Another class of bleaching agent stabilizers consists of tin-containing salts, such as tin nitrates, tin phosphates, and the like.

6. Bleaching Agent Activators.

Several bleaching agent activators are disclosed in the present invention such as radiant or thermal energy absorbable bleaching agent activators. The preferred qualities of bleaching agent activators include inertness to the bleaching agent and the ability to efficiently absorb radiant energy and cause the bleaching composition to heat up, thus activating the bleaching agent.

Inert particles that act as a heat sink may also be used. These particles may absorb radiant or conducted thermal energy in such a way so as to not substantially chemically react with the peroxide during application. Such particles may include metals coated with inert films or metal-filled plastic resins.

It has been found that radiant-energy absorbable, substantially conjugated hydrocarbons are the preferred bleaching agent activators since they appear to be significantly stable in the presence of peroxides. In other words, they themselves resist oxidation or bleaching in the presence of the bleaching agent.

Preferred bleaching agent activators are defined as substantially conjugated hydrocarbons such as multiple benzene structures, conjugated hydrocarbon chains, and combinations thereof that absorb portions of the electromagnetic spectrum and that have simple hydrogen, hydroxyl, or carboxylic groups attached to the structures and that act as energy-absorbing substances.

The preferred multiple benzene structures can be as simple as naptha-based structures or anthracene-based structures. Useful substantially conjugated hydrocarbons that are benzene structures that are radiant energy absorbing include 9,1 0-bis(phenylethynyl)-anthracene, perylene, naphtho[2,3-a]pyrene, trans-4,4'-diphenylstilbene, 9,10-diphenyl-anthracene, 5,12-bis(phenyethynyl)-napthacene, coronene, fluoranthene, and equivalents.

The known substantially conjugated bond hydrocarbon chains include caroteneoids, such as bixin, lycoxanthin, lycophil, canthaxanthin, capsanthin, cryptoxanthin, isomers of carotene, and lycopene. Of the known substantially conjugated hydrocarbons, 9,10-bis(phenylethynyl)-anthracene, perylene, and isomers of carotene are preferred. Of the known substantially conjugated hydrocarbons, carboxyl-substituted hydrocarbons are also preferred.

Less preferred aromatic compositions such as 7-diethylamino 4-methyl coumarin, henna, and alizarin are less stable compared to the above-defined substantially conjugated hydrocarbons. Henna, a red dye known for at least 4,000 years, is a double-ketonated naphtha hydroxide. Alizarin, a red dye, is a double-ketonated anthracene meta double hydroxide. Although 7-diethylamino 4-methyl coumarin, henna, and alizarin are less preferred, to the extent that one were to use these substances within a stable, one-part, pre-mixed bleaching composition, such a composition would certainly be within the scope of the present invention.

Other substantially conjugated hydrocarbon structures that resist oxidation by peroxides are within the skill of the routineer in the art to find during routine experimentation after consultation with the present invention disclosure or by practicing the invention.

The bleaching agent activators in the dental bleaching composition of the present invention will preferably not only efficiently absorb radiant energy but also preferably will not significantly contribute to bleaching agent decomposition while the composition sits on the shelf. In this way, the inventive bleaching composition will have substantially the same shelf life as a bleaching composition that does not include the bleaching agent activator when stored at an appropriately cool temperature. In addition to on-the-shelf inertness, it is also preferable that upon application of radiant energy, the bleaching agent activator itself does not substantially react with the oxidizer. The effect of a bleaching agent activator that resists oxidation during treatment is an increase in available activator relative to the remaining unreacted bleaching agent.

As radiant energy is applied to the dental bleaching composition, the bleaching agent activator begins to heat up and to accelerate the release of active oxygen from the bleaching agent.

Additionally, the bleaching agent activators of the present invention, particularly the preferred bleaching agent activators, could be used as colorants in hydrogen peroxide compositions such as dentifrices. Due to the stable quality of the preferred bleaching agent activators, they could be used a colorants for aesthetic reasons in otherwise uncolored hydrogen peroxide compositions.

7. General Properties.

To make the dental bleaching composition of the present invention a viable off-the-shelf product for dental professionals, hydrogen peroxide decomposition must be minimized during storage. Because hydrogen peroxide decomposition is accelerated by increasing temperatures, it is preferable to store the inventive dental bleaching composition at lower temperatures during long term storage (below room temperature, e.g., 4° C.). A preferred shelf life is at least about one month, where the amount of available bleaching agent is at least about 95% of the original concentration. For about two months, it is preferable for there to remain at least about 90% of the original available bleaching agent. For about three months, it is preferable for there to remain at least about 80% of the original available bleaching agent.

Obviously, it will generally always be preferable to have more stable systems in which most, if not all, of the bleaching agent remains active over the length of the shelf life. It has been observed that dental bleaching compositions of the present invention remained substantially undercomposed for about three months. For example, samples of the inventive dental bleaching composition were stored refrigerated for 92 days and there remained about 99% of the original available hydrogen peroxide. Samples of the inventive dental bleaching composition were stored refrigerated for 127 days and there remained above 98% of the original available hydrogen peroxide. Additionally, samples of the inventive dental bleaching composition were stored unrefrigerated for 92 days and there remained about 95% of the original available hydrogen peroxide. Because periodic testing of available hydrogen peroxide revealed slow decomposition of the bleaching agent after about three months, it is within the contemplation of the present invention that if refrigerated, uncontaminated, and light-shielded, the inventive dental bleaching composition will contain about 50%, preferably about 90%, and most preferably about 95% of the original available hydrogen peroxide for about one year.

Stability of a dental bleaching composition with about 35% available hydrogen peroxide, wherein the dental bleaching agent maintains at least about 85% of its original strength about one month after manufacture, is understood to be a composition that would contain about 30% available hydrogen peroxide.

The dental bleaching compositions of the present invention can be made such that they include from about 0.1% to about 90% available hydrogen peroxide; from about 0.05% to about 5% thickening agent; from about 0% to about 10% neutralizing agent; from about 5% to about 80% carrier; from about 0.01% to about 5% stabilizer; and from about 0.001% to about 3% bleaching agent activator.

More preferred dental bleaching compositions of the present invention can be made such that they include from about 10% to about 80% available hydrogen peroxide; from about 0.5% to about 4% thickening agent; from about 0.5% to about 5% neutralizing agent; from about 10% to about 75% carrier; from about 0.1% to about 3% stabilizer; and from about 0.02% to about 2% bleaching agent activator.

Most preferred dental bleaching compositions of the present invention can be made such that they include from about 20% to about 60% available hydrogen peroxide; from about 1% to about 3% thickening agent; from about 0.6% to about 3% neutralizing agent; from about 15% to about 65% carrier; from about 0.5% to about 2% stabilizer; and from about 0.05% to about 1% bleaching agent activator.

8. Examples of Preferred Dental Bleaching Compositions.

In order to more fully teach the present invention, the following examples are presented. The examples are intended to be illustrative only and are certainly not intended to imply that other embodiments not specified are not within the scope of the present invention. Bleaching compositions were prepared according to the present invention and included the components and amounts set forth as Examples 1–28, which are set forth below in Table 1.

In order to illustrate one exemplary manner of mixing together the components, attention is turned to Example 4, in which 254 g of propylene glycol was placed in a container and mixed with 12 g of PEMULEN® TR-1NF until homogenous. Next, stabilizers comprising 8 g each of edetate disodium and citric acid were mixed with water and added as stabilizers to the glycol-PEMULEN mixture to scavenge errant or residual metal ions. Thereafter, 4 g of beta carotene was added as the bleaching agent activator. Following addition of the bleaching agent activator, 705 g of 50% aqueous hydrogen peroxide was added. To the mixture was added 9 g of sodium hydroxide, 50% in water, and the resulting mixture was stirred until homogeneous. The other examples were mixed together in similar fashion, although the concentrations and identities of the components were altered in order to form the compositions as achieved.

Table 1 represents 28 exemplary compositions that were prepared according to the present invention and identified as Examples 1–28. In each sample, the bleaching agent was added in the form of aqueous hydrogen peroxide; therefore the number under the heading "$H_2O_2$" represents the net amount of hydrogen peroxide in the composition. Thus, the balance of the aqueous hydrogen peroxide was water. The thickener was PEMULEN® TR-1NF unless otherwise noted. The neutralizing agent was sodium hydroxide in 50% water. Other components are noted at the foot of Table 1.

TABLE 1

| Example | Active $H_2O_2$ | Water | Thickener | NaOH | Carrier | Stabilizer | Activator | Total |
|---|---|---|---|---|---|---|---|---|
| 1 | 30.25 | 30.25 | 1.2 | 0.9 | 36.4[1] | 1.0[2] | — | 100.0 |
| 2 | 30.5 | 30.5 | 1.5 | 0.8 | 36.7[3] | — | — | 100.0 |
| 3 | 30.5 | 30.5 | 1.2 | 0.9 | 36.9[4] | — | — | 100.0 |
| 4 | 35.25 | 35.25 | 1.2 | 0.9 | 25.4[1] | 1.6[5] | 0.4[6] | 100.0 |
| 5 | 35.25 | 35.25 | 1.2 | 0.9 | 27.4[3] | — | — | 100.0 |
| 6 | 35.25 | 35.25 | 1.2 | 0.9 | 27.4[4] | — | — | 100.0 |
| 7 | 35.25 | 35.25 | 1.2 | 0.9 | 27.4[6] | — | — | 100.0 |
| 8 | 35.25 | 35.25 | 1.2 | 0.9 | 27.3[3] | 1.0[2] | — | 100.0 |
| 9 | 35.25 | 35.25 | 1.2 | 0.9 | 27.2[3] | 0.2[2] | — | 100.0 |
| 10 | 35.25 | 35.25 | 1.2 | 0.9 | 26.4[1] | 1.0[2] | — | 100.0 |
| 11 | 35.25 | 35.25 | 1.2 | 0.9 | 26.4[4] | 1.0[2] | — | 100.0 |
| 12 | 35.25 | 35.25 | 1.2 | 0.9 | 26.0[1] | 1.0 | 0.4[7] | 100.0 |
| 13 | 35.25 | 35.25 | 1.2 | 0.9 | 26.0[1] | 1.4[8] | — | 100.0 |
| 14 | 35.25 | 35.25 | 1.2 | 0.9 | 25.9[1] | 1.5[9] | — | 100.0 |
| 15 | 35.25 | 35.25 | 1.2 | 0.9 | 25.5[1] | 1.5[9] | 0.4[10] | 100.0 |
| 16 | 35.25 | 35.25 | 1.2 | 0.9 | 25.8[1] | 1.5[9] | 0.1[10] | 100.0 |
| 17 | 35.25 | 35.25 | 1.2 | 0.9 | 25.5[1] | 1.8[11] | 0.1[10] | 100.0 |
| 18 | 35.25 | 35.25 | 1.2 | 0.9 | 25.7[1] | 1.6[12] | 0.1[10] | 100.0 |
| 19 | 35.25 | 35.25 | 1.2 | 0.9 | 25.7[1] | 1.8[13] | 0.1[10] | 100.0 |
| 20 | 35.25 | 35.25 | 1.2 | 0.9 | 25.0[1] | 2.3[14] | 0.1[10] | 100.0 |

TABLE 1-continued

| Example | Active H$_2$O$_2$ | Water | Thickener | NaOH | Carrier | Stabilizer | Activator | Total |
|---|---|---|---|---|---|---|---|---|
| 21 | 35.25 | 35.25 | 1.2 | 0.5 | 26.1[1] | 1.8[13] | 0.1[10] | 100.0 |
| 22 | 35.25 | 35.25 | 1.2 | 0.9 | 25.3[1] | 2.0[15] | 0.1[10] | 100.0 |
| 23 | 35.25 | 35.25 | 1.2 | 0.5 | 25.7[1] | 2.0[15] | 0.1[10] | 100.0 |
| 24 | 35.25 | 35.25 | 1.2 | 0.9 | 25.5[1] | 1.8[16] | 0.1[10] | 100.0 |
| 25 | 35.25 | 35.25 | 1.2 | 1.3 | 25.1[1] | 1.8[13] | 0.1[10] | 100.0 |
| 26 | 35.25 | 35.25 | 1.2 | 0.9 | 25.1[1] | 2.2[17] | 0.1[10] | 100.0 |
| 27 | 40.25 | 40.25 | 1.2 | 0.9 | 17.4[3] | — | — | 100.0 |
| 28 | 40.25 | 40.25 | 1.2 | 0.9 | 17.4[4] | — | — | 100.0 |

[1]Propylene glycol;
[2]Adipic acid:succinic acid 1:1;
[3]Distilled water;
[4]Glycerine;
[5]Edetate disodium:citric acid 1:1;
[6]Polyethylene glycol 300;
[7]Bis(phenylethynyl)-anthracene;
[8]Edetate disodium:adipic acid:succinic acid 0.8:1:1;
[9]Edetate disodium:adipic acid:succinic acid 1:1:1;
[10]Perylene;
[11]Edetate disodium:adipic acid:succinic acid 1.6:1:1;
[12]Edetate disodium:citric acid 1:1;
[13]Edetate disodium;
[14]Edetate disodium:adipic acid:succinic acid:citric acid 1:6:1:1:1;
[15]Edetate disodium:EDTA 1:1;
[16]Citric acid:EDTA 0.8:1;
[17]Edetate disodium:citric acid 1.75:1.

Of the foregoing, Example Nos. 2, 3, 5–7, 27 and 28 were prepared without using any stabilizer and without any bleaching agent activator. Upon measuring the concentration of active hydrogen peroxide over time, it was found that the hydrogen peroxide in these examples was not as stable as those formed with a stabilizer. The rate of decomposition was observed to increase as the concentration of hydrogen peroxide increased. This increased decomposition rate demonstrates the importance of the bleaching agent stabilizer in the event that a stable, one-part, pre-mixed bleaching composition is desired, particularly at higher concentrations of peroxide. These stabilizer-less compositions were also slow to react when irradiated with radiant energy and/or UV light from a standard dental curing light since they included no bleaching agent activator. Hence, in those cases where accelerated bleaching is desired, as opposed to slower but more steady bleaching, it is important to include the bleaching agent activator.

Of the foregoing examples set forth in Table 1, Example Nos. 1, 8–11, and 13–14 were made without any bleaching agent activator but did include a stabilizer, or a combination of stabilizers, according to the present invention. Upon measuring the concentration of active hydrogen peroxide over time it was found that the concentration of hydrogen peroxide in these examples remained above 90% of the original concentration after 28 days of storage. As in Example Nos. 2, 3, 5–9, 27 and 28, these compositions were slow to become activated when irradiated with visible and/or UV light using a commercial dental curing light. However, upon irradiating the compositions with heat energy using a heat lamp that emitted in the infrared range, accelerated decomposition of bleaching compositions within about 1 minute was observed.

Of the foregoing examples set forth in Table 1, Example Nos. 4, 12 and 15–26 were made to contain both a stabilizer and a bleaching agent activator according to the present invention. Upon measuring the concentration of active hydrogen peroxide over time it was found that the concentration of hydrogen peroxide in these examples remained above about 90% of the original concentration after 28 days of storage. Upon measuring the concentration of activator over time it was found that the concentration of the bleaching agent activator color remained virtually unchanged after 28 days of storage at an appropriate temperature, e.g. 4° C. Upon irradiating these compositions with visible and/or UV light using a commercial dental curing light, the compositions became activated. Because the concentration of activator remained stable over time, the slight drop in apparent stability of the hydrogen peroxide compared to compositions in which no activator was used was apparently due to the fact that the compositions were not prepared or stored in total darkness.

In order to more fully teach the invention, the following hypothetical examples are presented. While the compositions of the following examples were not actually physically mixed together, they were derived or extrapolated from actual mix designs and are based on the results determined by observing the behaviors of actual mix designs.

Examples 29–42 are made according to the mixing sequence set forth above for Example 4, except that the identities and concentrations of the various components are altered as set forth in Table 2 below.

TABLE 2

| Example | Active H$_2$O$_2$ | Water | Thickener | NaOH | Carrier | Stabilizer | Activator | Total |
|---|---|---|---|---|---|---|---|---|
| 29 | 0.1 | 0.1 | 1.2 | 0.2 | 97.3 | 1.0[2] | 0.1[10] | 100.0 |
| 30 | 3.5 | 3.5 | 1.2 | 0.8 | 90.0[1] | 1.0[2] | — | 100.0 |

TABLE 2-continued

| Example | Active $H_2O_2$ | Water | Thickener | NaOH | Carrier | Stabilizer | Activator | Total |
|---|---|---|---|---|---|---|---|---|
| 31 | 10 | 10 | 1.2 | 0.8 | 76.9[1] | 1.0[2] | 0.1[10] | 100.0 |
| 32 | 20 | 20 | 1.2 | 0.8 | 57.0[1] | 1.0[2] | — | 100.0 |
| 33 | 20 | 20 | 1.2 | 0.8 | 56.9 | 1.0[2] | 0.1[10] | 100.0 |
| 34 | 25 | 25 | 1.2 | 0.8 | 47.0 | 1.0[2] | — | 100.0 |
| 35 | 25 | 25 | 1.2 | 0.8 | 46.9 | 1.0[2] | 0.1[10] | 100.0 |
| 36 | 40.25 | 40.25 | 1.2 | 0.9 | 16.0[1] | 1.3[2] | 0.1[10] | 100.0 |
| 37 | 50.0 | 33.4 | 1.2 | 0.9 | 11.6[1] | 2.8[2] | 0.1[10] | 100.0 |
| 38 | 55.0 | 29.9 | 1.2 | 1.2 | 9.5[1] | 3.1 | 0.1[10] | 100.0 |
| 39 | 60.0 | 26.4 | 1.2 | 1.3 | 7.6[1] | 3.4 | 0.1[10] | 100.0 |
| 40 | 70.0 | 19.4 | 1.2 | 1.6 | 19.6[1] | 3.9 | 0.1[10] | 100.0 |
| 41 | 80.0 | 12.4 | 1.2 | 1.8 | — | 4.5 | 0.1[10] | 100.0 |
| 42 | 90.0 | 1.9 | 1.2 | 1.8 | — | 5.0 | 0.1[10] | 100.0 |

[1]Propylene glycol;
[2]Adipic acid:succinic acid 1:1;
[10]Perylene.

Of the foregoing compositions, Example Nos. 29, 32, 34 and 36–42 include both a stabilizer and a bleaching agent activator according to the present invention. The hydrogen peroxide concentration in these examples remains at a level of at least about 80% of the original concentration after 28 days of storage, while the bleaching agent activator color remains virtually unchanged after 28 days of storage. When irradiated, each of the compositions in these examples is activated.

B. Light Guides.

The structure and function of preferred light guides and their use in the methods of the invention can be best understood by reference to FIGS. 1–4. FIG. 1 illustrates light guide 30 of the present invention. Light guide 30 has a light directing member 32 having a configuration such that a dental arch may be received therein or placed in close proximity thereto. Light directing member 32 is preferably arcuate in order to maintain substantially the same distance from all the teeth being treated, although it may also be straight or angled to provide adequately directed light energy.

Light directing member 32 preferable includes a bottom portion 34 and a labial sidewall portion 36. Bottom portion 34 is a substantially flat member positioned substantially orthogonally to the labial sidewall portion 36 and configured so as to abut or be in close proximity to the incisal surfaces and any occlusal surfaces of selected teeth of the person being treated. Bottom portion 34 is useful for bracing or securing light guide 30 in a fixed position in relation to the dental arch when in operation. While it is preferable to include bottom portion 34 in light guide 30, the light guides and the methods disclosed herein may alternatively be practiced in the absence thereof.

Labial sidewall portion 36 is positioned and configured so as to abut or be in close proximity to the labial surfaces of the selected teeth. Labial sidewall portion 36 preferably has a curved shape substantially corresponding to the arc of a portion or all of the dental arch. Alternatively, labial sidewall portion 36 can have any geometric shape so long as light or other radiant energy can be adequately directed onto a person's teeth in order to activate or accelerate bleaching. Light directing member 32 and labial sidewall portion 36 may be configured to receive only a few teeth of a dental arch, configured to receive substantially the entire dental arch, or configured to receive any intermediate portion of a dental arch as desired.

Labial sidewall portion 36 has an inner surface 38 that is adjacent the labial surfaces of the selected teeth when the dental arch being treated is received into light directing member 32. Inner surface 38 has means for directing radiant energy onto the one or more teeth that have been treated with the bleaching composition. As but one example of such means for directing or emitting radiant energy, one or more light-emitting panels 40 are arrayed along inner surface 38 as depicted in FIG. 1. Light-emitting panels 40 are at least partially transparent to light and are preferably substantially transparent to light and other radiant energy produced by light guide 30. Light-emitting panels 40 may consist of, for example, glass, plastics, or other transparent optical materials. Light-emitting panels 40 are positioned upon inner surface 38 to be adjacent to the labial surfaces of the teeth being treated. It will be understood that light-emitting panels 40 may consist of any number of panels. For example, there may be only one panel 40 on inner surface 38 corresponding to one or more teeth or, alternatively, there may be multiple panels 40, each corresponding to an individual tooth or group of teeth to be treated. Light-emitting panels 40 may be round, square, rectangular, elongated along a portion of all of inner surface 38, or may have any other suitable shape that is capable or focusing radiant energy as desired to effect accelerated bleaching. Other light-emitting members can be used to irradiate a person's teeth with radiant energy.

Labial sidewall portion 36 and light-emitting panels 40 are preferably configured in relation to the treated teeth so that radiant energy is efficiently directed on the treated teeth without substantial irradiation of surrounding gingival tissues and other oral and facial tissues of the person being treated. This serves to eliminate a significant portion of the discomfort that has been associated with prior art radiant energy sources, such as curing lights or lamps.

Figure 2:
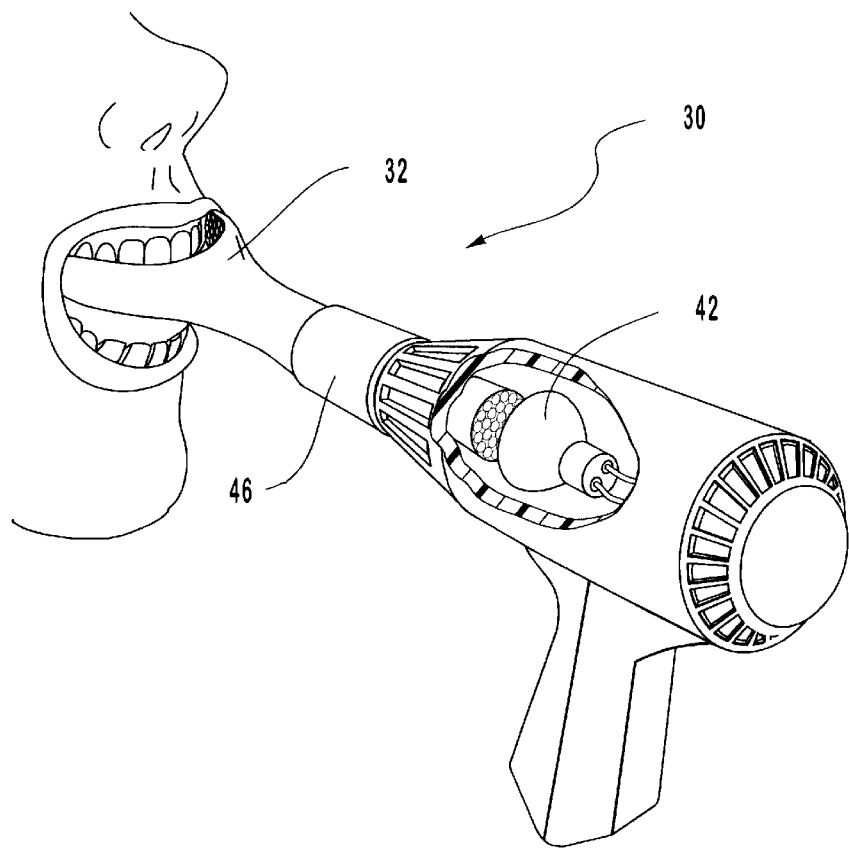
FIG. 2 illustrates use of the light guide of FIG. 1 wherein the light guide is in close proximity to a person's dental arch.

Light guide 30 includes means for generating radiant energy that is preferably positioned to be outside the person's mouth during operation of light guide 30. Light source 42, seen in FIG. 2, is but one example of such means for generating radiant energy. Light source 42 preferably generates light with wavelengths concentrated, for example, within the ultraviolet region or in the blue end of the visible region of the ultraviolet spectrum. In particular, light source 42 preferably generates radiant energy having wavelengths that are readily absorbed by the photosensitive bleaching agent activator of the bleaching composition. Moreover, it will be understood that higher-energy, lower-wavelength light is somewhat preferable because such frequencies contain more potential heat energy compared to lower energy frequencies. However, the light frequency should not be so high as to produce uncomfortable or unhealthy effects in the person being treated. Of course, infrared heat can also be used although it is generally more difficult to focus.

Light guide 30 also includes means for transmitting radiant energy from the means for generating the radiant energy to the means for directing the radiant energy onto the treated teeth. One example of such means for transmitting radiant energy comprises optical fibers 44, as depicted in FIG. 1, which extend from light source 42, through neck 46 and to light-emitting panels 40. Accordingly, radiant energy generated by light source 42 may be efficiently delivered to the treated teeth without undue loss of energy in transit.

Referring now to FIG. 2, the light guide is shown positioned within the mouth of a person being treated. The light guide receives the upper dental arch in FIG. 2. However, light guide 30 may be configured to treat all or part of the lower dental arch in an alternative embodiment (not shown). In still another embodiment (not shown), a light guide may be provided that is able to treat all or part of both the upper and lower dental arches at the same time. In another embodiment, a light guide may be provided that is able to treat selected teeth of the upper dental arch. As can be seen, neck 46 of light guide 30 extends away from the person being treated when the dental arch is received by light directing member 32.

Figure 3:
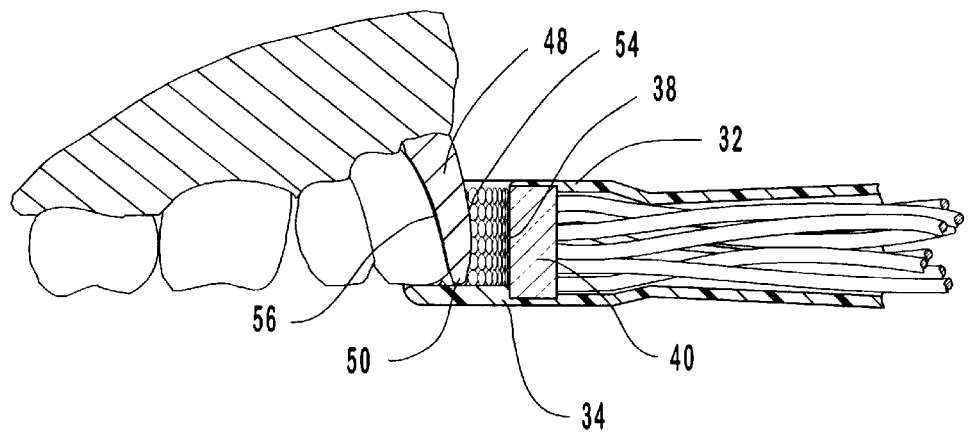
FIG. 3 is an elevational cross section of the light guide of FIG. 1. The light guide is in close proximity to the dental arch such that radiant energy may be directed onto at least one of the person's teeth.

FIG. 3 further illustrates the relative positioning of light directing member 32 and the dental arch, including tooth 48, of the person being treated. Tooth 48 may be, for example, a highly visible upper incisor. Light directing member 32 is positioned to abut or to be adjacent the dental arch. Bottom portion 34 of light directing member 32 abuts or is adjacent the incisal surfaces 50 and any occlusal surfaces of the teeth that are to be treated. As seen in FIG. 3, bottom portion 34 is positioned under tooth 48 when the upper dental arch is treated. Conversely, when the light guide is configured to treat a lower dental arch, bottom portion 34 will be positioned over the teeth of the lower dental arch.

When the light guide is placed in its operating position in the mouth of the person being treated, inner surface 38 is in close proximity to labial surface 54 of tooth 48. Such positioning allows radiant energy to be efficiently directed onto the treated surfaces of tooth 48. In addition, light directing member 32 preferably has an open lingual portion that is characterized by the absence of a sidewall or other structure adjacent the lingual surface 56 of tooth 48. Accordingly, the open lingual portion of light directing member 32 is configured such that lingual surface 56 of tooth 48 is substantially unenclosed when the light guide receives the dental arch.

As seen in FIG. 3, bottom portion 34 and labial sidewall portion 36 may be substantially orthogonal relative to one another. Together, bottom portion 34 a labial sidewall portion 36 constrain movement of the light guide in two directions. For example, bottom portion 34 substantially prevents the light guide from moving beyond incisal surface 50 in a direction perpendicular to the plane defined by bottom portion 34. Likewise, labial sidewall portion 36 substantially prevents the light guide from moving beyond labial surface 54 in a direction parallel to the plane defined by bottom portion 34. As a result, the configuration of light directing member 32 provides some degree of support for light guide 30 during operation thereof.

Figure 4:
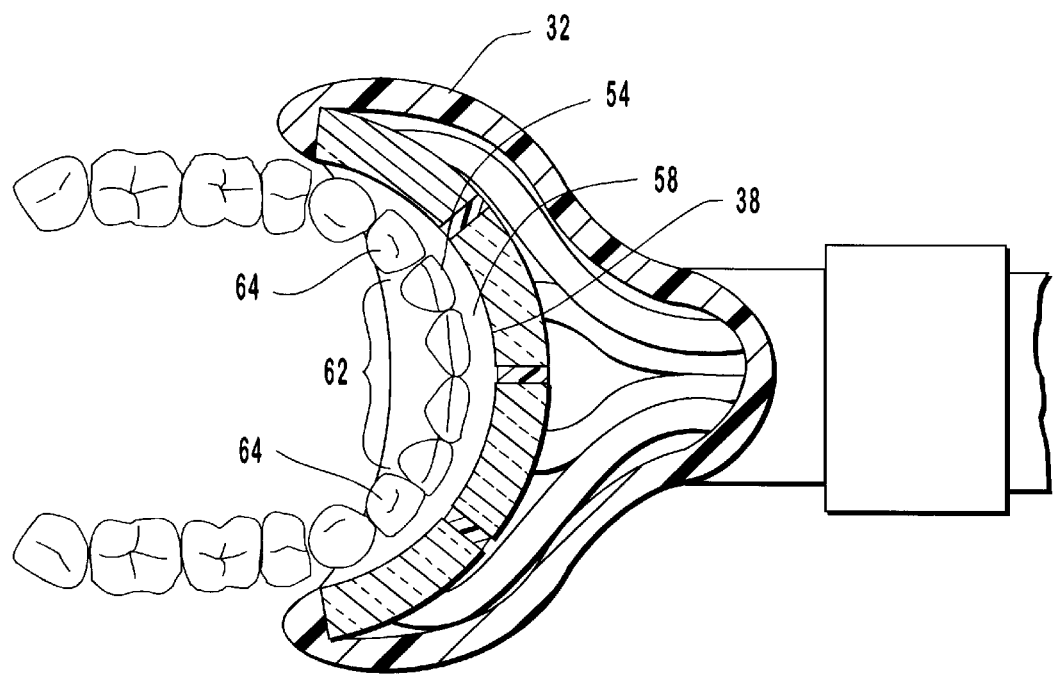
FIG. 4 is a top view of the arcuate member of the light guide of FIG. 1, showing the relative positioning of the light guide and the dental arch.

FIG. 4 illustrates the relative positioning of light directing member 32 and a dental arch 60 received therein. While light directing member 32 is preferably shaped to correspond to the arc of the dental arch, inner surface 38 will generally not conform precisely to labial surfaces 54, but a gap or space 58 will typically exist therebetween. Of course, certain portions of inner surface 38 may be in contact with labial surface 54. However, a substantial portion of inner surface 38 will generally be displaced at least a small distance from labial surface 54.

FIG. 4 is also presented to emphasize the fact that light directing member 32 may be configured as desired to be in close proximity with any or all of the teeth of dental arch 60. In practice, there will usually be the greatest interest in bleaching the most visible portions of dental arch 60. Accordingly, light directing member 32 will preferably be configured for being placed in close proximity to at least the incisor portion 62 of dental arch 60. More preferably, light directing member 32 will generally be configured for being placed in close proximity to canine portions 64 of dental arch 60, in addition to the incisor portion 62. As defined herein, "incisor portion" includes the incisors of a dental arch, and "canine portion" includes the canines of a dental arch. In other situations, as many as all of the teeth of dental arch 60 may be treated, in which case, light directing member 32 should be large enough to be placed in close proximity with substantially all of the teeth of dental arch 60.

Although there is naturally more widespread interest in treating the labial surfaces of the most visible teeth, the invention should certainly not be seen as being limited thereto. Instead, the invention extends to light guides and methods for treating any desired teeth and desired tooth surfaces.

C. Methods of Using Light Guide and Bleaching Composition.

Figure 5:
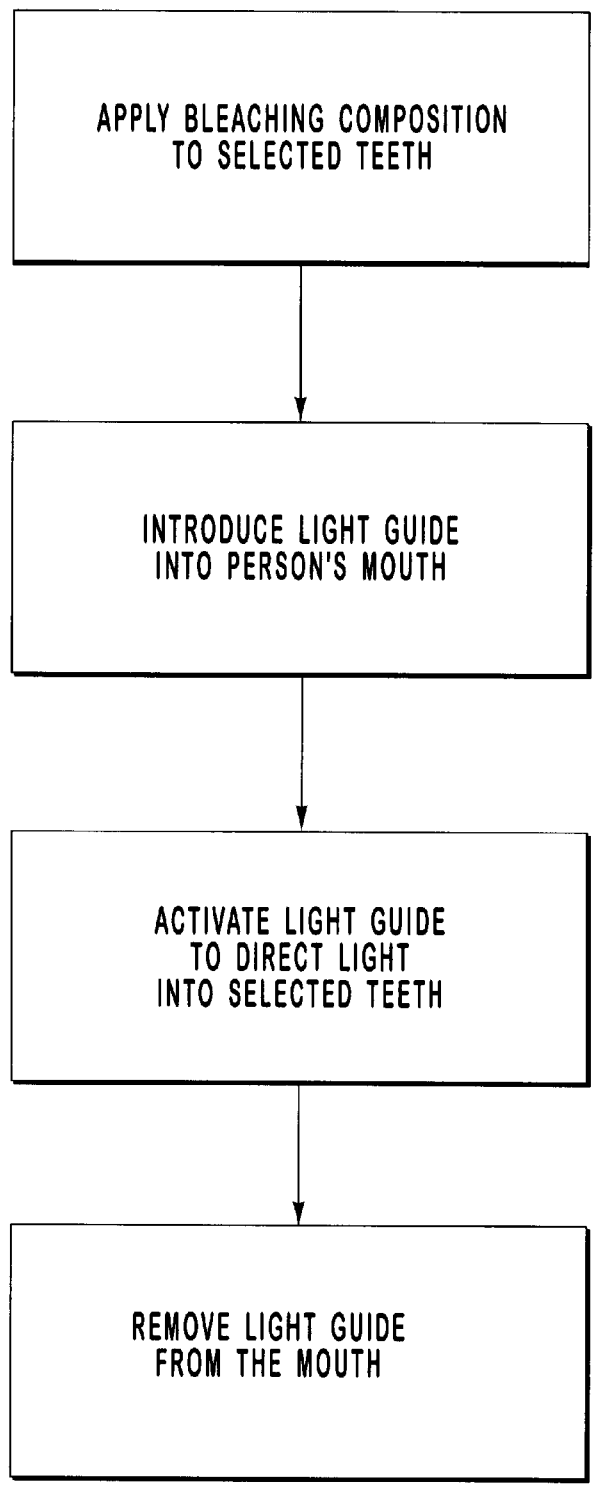
FIG. 5 is a flow chart depicting the steps of a method of bleaching teeth using the light guide.

In light of the foregoing inventive features of the dental compositions and light guides of the present invention, the method for bleaching teeth is performed in the dental operatory under ordinary conditions. In a preferred method, which may be understood in reference to FIG. 5, the dental professional applies a layer of the inventive dental bleaching composition on the labial surfaces of as many of the teeth as are desired to be bleached. For example, the dental bleaching composition may advantageously be loaded into and dispensed from a syringe onto the person's teeth.

Next, the light guide is introduced into the mouth by placing the arcuate member adjacent to either the upper or lower dental arch, or over both simultaneously if configured for this use. When the light guide is in position, the light guide is activated to transmit radiant energy from the light source through the light-emitting panels onto the selected teeth. The light guide remains in a fixed position during the application of the radiant energy.

Rapid bleaching is carried out as radiant energy, such as visible and/or ultraviolet light, is absorbed by the bleaching agent activator and by the treated teeth. It is believed that the radiant energy excites the dental bleaching activator, which causes the molecular bonds within the activator to vibrate vigorously and raise the temperature of the composition. Heating the dental bleaching composition causes the accelerated release of free radical oxygen from the dental bleaching agent. The rate of activation can be controlled by the amount of radiant energy that is used. The radiant energy is applied to the treated teeth for an amount of time that results in a desired degree of bleaching.

Since the light guide simultaneously directs radiant energy onto at least all treated teeth of one dental arch, the practitioner can ensure that all treated teeth receive radiant energy for substantially the same amount of time. Moreover, the overall duration of treatment may be easily monitored. Upon completion of the desired level of bleaching, the light guide is removed from the mouth. Depending on the results of the foregoing steps, the method may be repeated as needed or desired.

In the case where either the upper or lower arches are initially darker than the other dental arch of the person, it may be advantageous to first treat the darker of the two dental arches, or portions thereof, in order to first equalize the coloration of all of the person's teeth. Thereafter, once substantial equalization of coloration has been achieved, it may be advantageous to treat both the upper and lower dental arches simultaneously to ensure more even bleaching of all the person's teeth.

The methods and systems of the present invention may be used with other dental bleaching compositions in addition to those specifically disclosed herein. While preferred bleaching compositions include the stable, one-part, dental bleaching compositions disclosed herein, the methods and systems of the invention may also be advantageously conducted using other bleaching compositions. For example, any bleaching composition that may be used in dental applications and that can provide an increased bleaching rate in response to the application of radiant energy is contemplated for use with the preferred light guides, including the light guide with the arcuate member that is disclosed herein.

The bleaching methods of the present invention are not limited to any particular lightguide or radiant energy source, although the inventive light guides are certainly preferred. Accordingly, other means for applying radiant energy to tooth surfaces other than those specifically disclosed herein may also be used with the inventive bleaching compositions. While preferred radiant energy sources include the light guides having an arcuate member disclosed herein, the methods of the invention may also be advantageously conducted with other radiant energy sources. Such light guides or other means for applying radiant energy that are contemplated under the invention include, but are not limited to, heat lamps, conventional dental light guides, laser devices, and the like.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for bleaching a person's teeth comprising:
    (a) providing a dental bleaching composition that comprises at least one dental bleaching agent and at least one dye that is not entirely bleached by the dental bleaching agent prior to use of the dental bleaching composition and which, when exposed to radiant energy, absorbs at least a portion of said radiant energy and causes the dental bleaching composition to heat up and thereby accelerate bleaching activity of the dental bleaching
    (b) applying the dental bleaching composition to one or more of the person's teeth; and
    (c) directing radiant energy to the dental bleaching composition applied to the one or more teeth by means of a dental curing lamp so as to cause the dental bleaching composition to heat up through absorption of at least a portion of said radiant energy by the dye, thereby causing the bleaching agent to impart accelerated bleaching of the one or more teeth.

2. A method as defined in claim 1, wherein the dye comprises an organic dye which is a substantially conjugated hydrocarbon.

3. A method as defined in claim 2, wherein the substantially conjugated hydrocarbon is selected from the group consisting of naphtha-based compounds, anthracene-based compounds, and mixtures thereof.

4. A method as defined in claim 2, wherein the substantially conjugated hydrocarbon is selected from the group consisting of 9,10-bis(phenylethynyl)-anthracene; perylene; naphtho(2,3-a)pyrene; trans-4,4'-diphenylstilbene; 9,10-diphenylanthracene; 5,12-bis(phenyethynyl)-naphthacene; coronene; fluoranthene; and mixtures thereof.

5. A method as defined in claim 2, herein the substantially conjugated hydrocarbon is selected from the group consisting of carotenoids, bixin, lycoxanthin, lycophil, canthaxanthin, capsanthin, cryptoxanthin, isomers of carotene, lycopene, and mixtures thereof.

6. A method as defined in claim 1, wherein the dental bleaching composition further includes a less stable dye selected form the group consisting of 7-diethylamino 4-methyl coumarin, henna, alizarin, and mixtures thereof.

7. A method as defined in claim 1, wherein the bleaching agent comprises at least one of carbamide peroxide, sodium perborate, or aqueous hydrogen peroxide.

8. A method as defined in claim 1, wherein the bleaching composition further includes a bleaching agent stabilizer.

9. A method as defined in claim 1, wherein the dental bleaching composition comprises a stable, one-part composition.

10. A method as defined in claim 1, wherein the dental bleaching agent is included in an amount in a range from about 0.1% to about 90% by weight of the dental bleaching composition.

11. A method as defined in claim 1, wherein the dental bleaching agent is included in an amount in a range from about 10% to about 80% by weight of the dental bleaching composition.

12. A method as defined in claim 1, wherein the dental bleaching agent is included in an amount in a range from about 20% to about 60% by weight of the dental bleaching composition.

13. A method for bleaching a person's teeth comprising:
    (a) providing at least one dental bleaching composition that includes at least one dental bleaching agent and at least one dye selected form the group consisting of bixin; lycoxanthin; lycophil; canthaxanthin; capsanthin; cryptoxanthin; isomers of carotene; lycopene; 9,10-bis(phenylethynyl)-anthracene; perylene; naphtho (2,3-a)pyrene; trans-4,4'-diphenylstilbene; 9,10-diphenylanthracene; 5,12-bis(phenyethynyl)-naphthacene; coronene; fluoranthene; naphtha-based compounds; anthracene-based compounds; and mixtures thereof;
    (b) applying the dental bleaching composition to one or more of the person's teeth; and
    (c) exposing the dental bleaching composition applied to the one or more teeth to at least one radiant energy source so as to cause the dental bleaching composition to heat up through absorption of at least a portion of said radiant energy by the dye, thereby causing the bleaching agent to impart accelerated bleaching of the one or more teeth.

14. A method as defined in claim 13, wherein the radiant energy source comprises a dental curing lamp.

15. A method as defined in claim 13, wherein the radiant energy source comprises a laser.

16. A method as defined in claim 13, wherein the radiant energy source comprises a light guide that includes a light directing member configured to come into close proximity to labial surfaces of at least a portion of the person's teeth and a radiant energy generator communicating with one or more light emitting members disposed within an inner surface of the light directing member so that the light emitting members are capable of emitting light when the light guide is selectively activated.

17. A method as defined in claim 16, wherein the light guide includes an arcuate member configured to come into close proximity with at least one of a portion of the person's upper teeth and a portion of the person's lower teeth.

18. A method as defined in claim 16, wherein the radiant energy generator transmits radiant energy to the one or more light-emitting members by means of optical fibers communicating between the radiant energy generator and the light-emitting members.

19. A method as defined in claim 16, wherein the light directing member is configured to treat at least a portion of one of (a) the person's upper dental arch or (b) the person's lower dental arch.

20. A method for bleaching a person's teeth comprising:

(a) providing at least one dental bleaching composition that includes at least one dental bleaching agent and at least one dye selected form the group consisting of 9,10-bis(phenylethynyl)-anthracene, perylene, isomers of carotene, and mixtures thereof;

(b) applying the dental bleaching composition to one or more of the person's teeth; and (c) exposing the dental bleaching composition applied to the one or more teeth to at least one radiant energy source so as to cause the dental bleaching composition to heat up through absorption of at least a portion of said radiant energy by the dye to thereby cause the bleaching agent to impart accelerated bleaching of the one or more teeth.

21. A method for bleaching a person's teeth comprising:

(a) providing a dental bleaching composition that comprises at least one dental bleaching agent and at least one dye that is not entirely bleached by the dental bleaching agent prior to use of the dental bleaching composition and which, when exposed to radiant energy, absorbs at least a portion of said radiant energy and causes the dental bleaching composition to heat up and thereby accelerate bleaching activity of the dental bleaching agent;

(b) applying the dental bleaching composition to one or more of the person's teeth; and (c) directing radiant energy to the dental bleaching composition applied to the one or more teeth by means of at least one of a dental curing lamp or a light guide so as to cause the dental bleaching composition to heat up through absorption of at least a portion of said radiant energy by the dye, thereby causing the bleaching agent to impart accelerated bleaching of the one or more teeth.

* * * * *

UNITED STATES PATENT AND TRADEMARK OFFICE
CERTIFICATE OF CORRECTION

PATENT NO. : 6,391,283 B1
DATED : May 21, 2002
INVENTOR(S) : Steven D. Jensen and Dan E. Fischer It is certified that error appears in the above-identified patent and that said Letters Patent is hereby corrected as shown below:

Column 19,
Line 61, after "bleaching" insert -- agent; --

Column 20,
Line 50, after "dye selected" change "form" to -- from --

Column 21,
Line 30, after "dye selected" change "form" to -- from --

Signed and Sealed this

First Day of July, 2003

JAMES E. ROGAN
*Director of the United States Patent and Trademark Office*